(12) United States Patent
Chu et al.

(10) Patent No.: US 8,778,361 B2
(45) Date of Patent: Jul. 15, 2014

(54) CANINE TUMOR CELL AND ALLOGENEIC DENDRITIC CELL FUSED VACCINE AND METHOD FOR PREPARING THE SAME

(75) Inventors: Rea-Min Chu, Taipei (TW); Chien-Chun Pai, Taipei (TW); Tien-Fu Chuang, Taipei (TW)

(73) Assignee: National Taiwan University, Taipei (TW)

( * ) Notice: Subject to any disclaimer, the term of this patent is extended or adjusted under 35 U.S.C. 154(b) by 177 days.

(21) Appl. No.: 12/483,735

(22) Filed: Jun. 12, 2009

(65) Prior Publication Data

US 2010/0227395 A1 Sep. 9, 2010

(30) Foreign Application Priority Data

Mar. 9, 2009 (TW) ................................ 98107651 A

(51) Int. Cl.
| | |
|---|---|
| *A61K 35/14* | (2006.01) |
| *C12N 5/0784* | (2010.01) |
| *C12N 5/09* | (2010.01) |
| *C12N 5/16* | (2006.01) |
| *C12N 15/06* | (2006.01) |
| *A61K 39/00* | (2006.01) |

(52) U.S. Cl.
CPC ........... *C12N 5/16* (2013.01); *A61K 2039/5154* (2013.01); *A61K 39/001* (2013.01); *A61K 2039/5152* (2013.01)
USPC ........ 424/277.1; 424/534; 435/346; 435/374; 435/450

(58) Field of Classification Search
None
See application file for complete search history.

(56) References Cited

PUBLICATIONS

Rivera et al, Comparative Medicine, 2005, vol. 55, pp. 335-343.*
Roos et al, 'Control of Membrane Fusion in Polyethylene Glycol-Resistant Cell Mutants', In: "Cell Fusion", 1987, A. Sowers, Ed., Figure 5, p. 135, and sections 3.3, pp. 139-141).*
de Carvalho et al, Pathologie Biologie, 2006, vol. 54, pp. 85-93.*
Bird et al (Veterinary Immunology and Immunopharmacology, 2008, vol. 123, pp. 289-304).*
Tamura et al (The Veterinary Journal, 2008, vol. 175, pp. 126-129).*
Chu, Host/Cancer Interactions and Cell-based Cancer Immunology, 2008, Shanghai China, BIT Life Sciences 1st Annual World Cancer Congress.
Ya-Wen Hsiao et al., "Effect of tumor infiltrating lymphocytes on the expression of MHC molecules in canine transmissible venereal tumor cells,"Veterinary immunology and immunopathology, Jan. 29, 2002, pp. 19-27, vol. 87. (See highlighted: pp. 20-21).
Mayu Isotani et al., "Efficient Generation of Canine Bone Marrow-Derived Dendritic Cells", J. Vet. Med. Sci., Apr. 2006, pp. 809-814, vol. 68(8). (See highlighted: pp. 809-810).
Chien-Chun Pai et al., "Immunopathogenic behaviors of canine transmissible venereal tumor in dogs following an immunotherapy using dendritic/tumor cell hybrid", Veterinary immunology and immunopathology, Oct. 2010, pp. 187-199, vol. 139.

* cited by examiner

*Primary Examiner* — Karen Canella
(74) *Attorney, Agent, or Firm* — WPAT, P.C.; Anthony King

(57) ABSTRACT

The present invention provides a dendritic cell-based vaccine by fusing a canine tumor cell and an allogeneic dendritic cell, and a method for preparing the same. The fusion cells expressing canine tumor antigens are generated by fusing canine bone marrow-derived dendritic cells and canine tumor cells. The canine immune system can be induced to produce tumor specific T lymphocytes and natural killer cells when the fusion cells used as a vaccine is injected into a canine body.

4 Claims, 17 Drawing Sheets

Control

Experiment Group

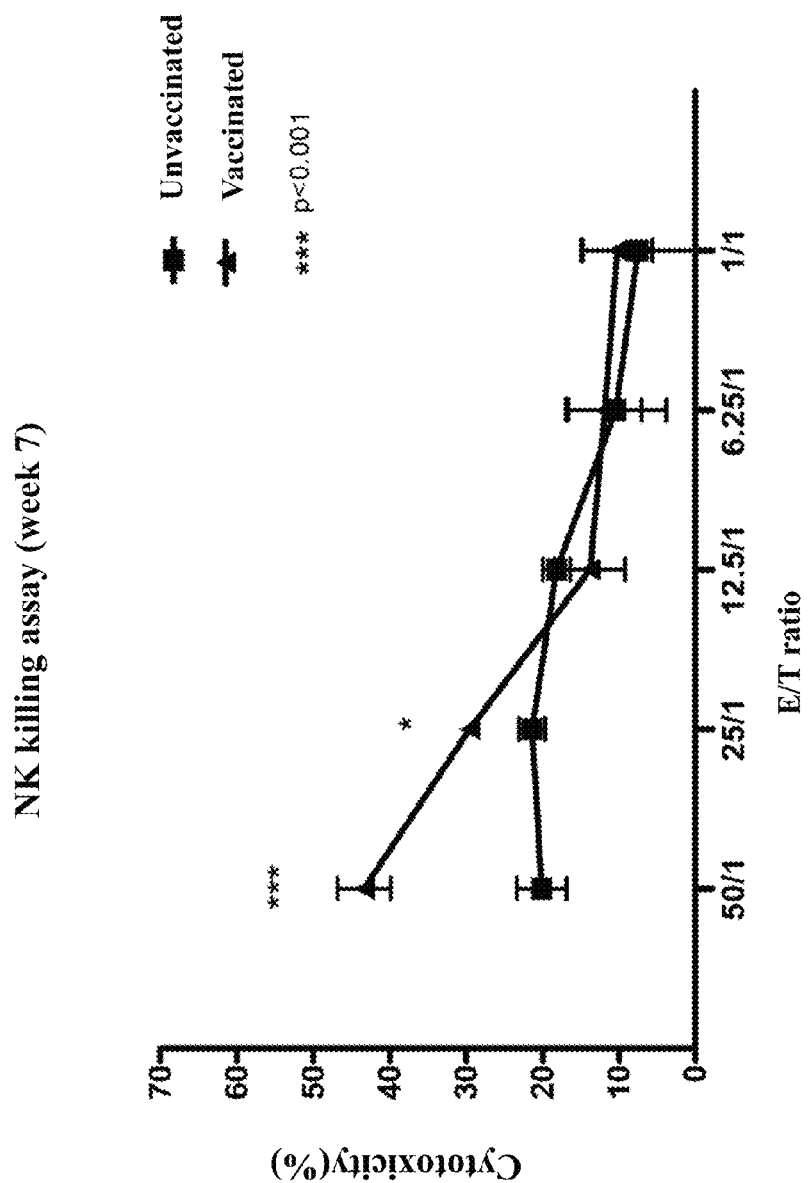

CANINE TUMOR CELL AND ALLOGENEIC DENDRITIC CELL FUSED VACCINE AND METHOD FOR PREPARING THE SAME

FIELD OF THE INVENTION

The present invention relates to a dendritic cell-based vaccine composed of fusions of a canine tumor cell and an allogeneic dendritic cell, and a method for preparing the same to induce the canine immune system to defend against canine tumor growth.

BACKGROUND OF THE INVENTION

Canine transmissible venereal tumor (CTVT) is transmitted via mating, wound-to-wound or saliva contact. The growth model of CTVT includes progressive phase (P phase), steady phase (S phase), and regressive phase (R phase). Major histocompatibility complex (MHC) molecule expresses on the surface of CTVT cells. Tumor cells lack MHC antigen during P phase, while both MHC classes I and II are increased dramatically during R phase (the $12^{th}$ week after inoculation), and they are continued to increase till regression of CTVT. The MHC molecules expressed are important for helper CD4 T cells and cytotoxic T lymphocytes in tumor recognition. The low amount of MHC of tumor during P phase evades the attack of the host immune system. On the other hand, TGF-β highly secreted by tumors during P phase can inhibit both NK cells and dendritic cells (DCs), which causes tumor related antigens were not presented to T cells, followed by immune tolerance. The mechanism is summarized in FIG. 1, where TGF-β highly secreted by CTVT tumors inhibits the IFN-γ-induced MHC expression, and therefore inhibit the killing activity since no MHC is expressed. However, tumor infiltrating lymphocytes (TIL) in host secreted large amount of IL-6 to counteract these effects in an unknown mechanism. The functions of IFN-γ and mononuclear cells are recovered, and CTVT cells are killed by T cells and NK cells, followed by entering the R phase.

In addition, dendritic cells can be inhibited by TGF-β secreted by CTVT. DCs are the most important antigen presenting cells (APCs). Part of the tumor cells will be dead during the early stage of tumor growth due to the genetic instability and unbalanced nutrients and release tumor associated antigen. The tumor associated antigen will be ingested by immature dendritic cells (iDCs) through endocytosis. These iDCs migrate to lymph nodes to become mature dendritic cells (mDCs) with the help of chemochytokine receptor 7 (CCR7). High levels of co-stimulatory molecules such as CD80/CD83/CD86 will be expressed in mDCs and effectively activate native CD4+ T cells, followed by activate CD8+ T cells to become cytotoxic T cells to kill tumor cells specifically. On the other hand, CD8 T cell can be activated by DCs directly through cross-priming to kill tumor cells. However, high concentration of TGF-β secreted by tumor inhibits monocyte-derived dendritic cells, including lowering the surface molecules of DCs such as CD80/CD86/MHC II, or lowering the ability of antigen endocytosis and antigen presentation. Then the specific killing ability will be lost since DCs are unable to present antigens to T cells effectively. Therefore, activating DCs cells effectively to present antigens for T cells and killing tumor cells after recognition are key issues for the study. In addition, how to present the unknown antigens to T cells is also an important issue since most of the tumor antigens are unknown.

SUMMARY OF THE INVENTION

In order to fulfill the abovementioned needs, the inventor invented a novel fusion cell composed of a canine tumor cell and an allogeneic dendritic cell, and a method for preparing the same.

A primary object of the present invention is to provide a fusion cell composed of a canine tumor cell and an allogeneic dendritic cell to induce a canine immune system to defend against a canine tumor cell.

Another object of the present invention is to provide a fusion cell composed of a canine tumor cell and an allogeneic dendritic cell to be used in preparation of a canine tumor vaccine.

Yet another object is to provide a method for preparing a fusion cell composed of a canine tumor cell and an allogeneic dendritic cell.

To accomplish the abovementioned purposes, the fusion cell in the present invention composed of a canine tumor cell and an allogeneic dendritic cell was obtained by fusing a dendritic cell from a bone marrow and a canine tumor cell. The dendritic cell is an antigen presenting cell (APC), and wherein the dendritic cell is a mature allogeneic dendritic cell. The fusion cell can express all the canine tumor antigens and present antigens as the dendritic cell. Therefore, the fusion cell can activate helper T cell and cytotoxic T cell in immune system effectively. In addition, the fusion cell can activate NK cell to kill a tumor cell.

A method for preparing the fusion cell composed of a canine tumor cell and an allogeneic dendritic cell according to the present invention comprising:
(a) isolating a mononuclear cell from a canine bone marrow and culturing the mononuclear cell to an immature dendritic cell (iDC);
(b) culturing the immature dendritic cell (iDC) to a mature dendritic cell (mDC);
(c) fusing the mature dendritic cell and the canine tumor cell by supplementing polyethylene glycol (PEG) in serum free medium, and centrifuging the cell after proper steps and culturing to form the fusion cell.

The step (a) further comprises culturing the mononuclear cell with a dendritic cell culture medium containing RPMI 1640, 10% FCS, IL-4(20 ng/ml), and GM-CSF (20 ng/ml).

In addition, the fusion cell is formed by electrofusion.

The fusion cell prepared according to the present invention is used as a canine tumor vaccine for therapy.

The present invention is further explained in the following embodiment illustration and examples. The present invention disclosed above is not limited by these examples. The present invention may be altered or modified a bit and all such variations are within the scope and spirit of the present invention.

BRIEF DESCRIPTION OF THE DRAWINGS

FIG. 11C shows the results of natural killer cells expressed in canine tissues.

DETAILED DESCRIPTION

Figure 1:
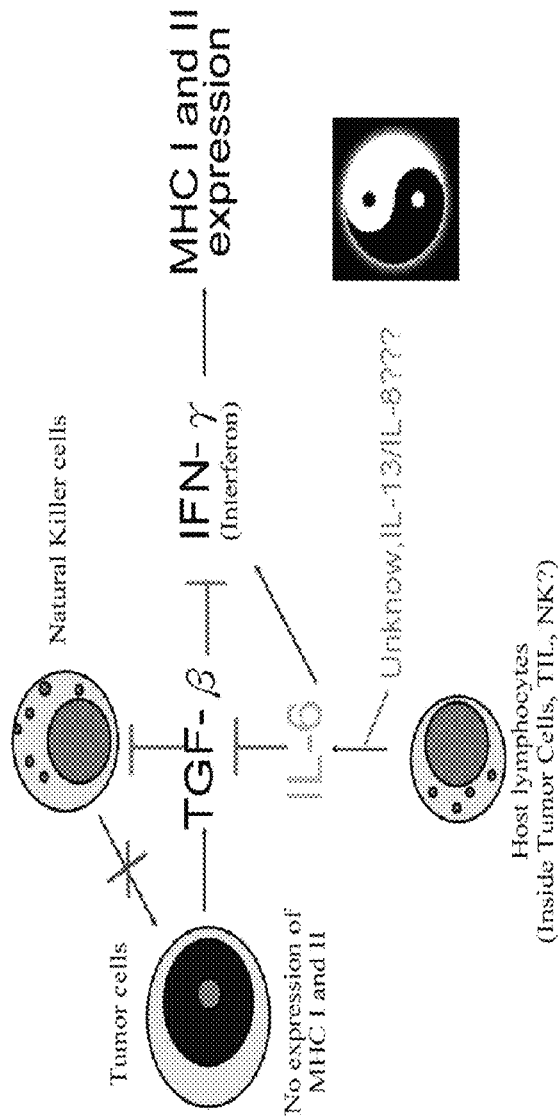
FIG. 1 shows the interaction diagram of a host and a canine CTVT tumor.

Generation of dendritic cells (DCs) is obtained from differentiation of peripheral blood mononuclear cells at present. Somehow the yield of this way is low, which is not suitable for development of vaccine. Therefore, the present invention induced the precursor cells from bone marrow to differentiate to DCs by supplementing with proper growth factors. This high yield method provides enough DCs for vaccine research. Table 1 compares the yields of DCs obtained from bone marrow and from peripheral blood mononuclear cells.

TABLE 1

| Subject | Aspiration (mL) | MNC ($\times 10^7$) | Cells obtain ($\times 10^7$) | Yield efficiency ($\times 10^8$/mL) |
| --- | --- | --- | --- | --- |
| BMDC | 10 | 41.93 (12.28)* | 41.06 (13.74)* | 4.1 (1.37)* |
| PBDC | 10 | 2 | 0.08 | 0.008 |

*mean % (Standard deviation)
BMDC: bone marrow derived-dendritic cells
PBDC: peripheral blood derived-dendritic cells The difficulty of DCs production limits the application in clinical therapy. The mononuclear cells from bone marrow were induced to differentiate into DCs in vitro in the present invention, and the yield was increased 20 folds in comparison to the peripheral blood derived DCs. Example 1 of the present invention prepared a CTVT fusion cell obtained by fusing allogeneic dendritic cell from bone marrow and Canine Transmissible Veneral Tumor (CTVT). Other fusion examples using DCs and tumor cells such as melanoma, breast cancer or lymphoma fusion cells can also be prepared to fight against each canine tumor respectively. On the other hand, bone marrow from CTVT dogs are not good source for fusion because most of the DCs from CTVT dogs are damaged by tumor and the risks associated with anesthesia and surgery are high. A healthy dog becomes a better source for DCs. In addition, allogeneic DCs from healthy dogs show strong ability in activating T cells in order to induce immune system in hosts and kill the tumor.

Antigen expression levels can be screened in DCs from bone marrow in different growth stage. Immature DCs (iDC) are irregular in shape, while matured DCs have a striking dendritic-shape. The maturation of DCs could be determined by detecting surface markers using flow cytometry and real-time PCR. Immature or mature DCs were stained with FITC-conjugated anti-goat IgG antibodies, mixed with FACS, followed by analysis of FACS-Calibur flow cytometry. The cytometer generally consists of four main components: a fluidic system, an optical system, a sorting system and an electronic system. Cells to be assayed passed the laser beam area through the fluidic system in an order. When cells pass through the laser intercept, they scatter laser light. This signal will be received and amplified by the appropriate detectors. The amplified signal is analyzed by a computer and displayed in figures. Cells with different marks are screened through the sorting system. The signals include scattered and fluorescent light. The intensity of scattered light reflects the size and morphology of cells. Different color is emitted according to the wavelength of the fluorescent light. This fluorescent light reflects various cell biological characteristics in different experimental systems.

The expression of CD80, CD83 and CD86 in mDCs and iDCs from bone marrow is shown in FIG. 1. RNA extracted from mDCs and iDCs was reverse transcribed into complementary DNA, and the opposite strand was also synthesized to form double stranded DNA. The fluorescent intensity emitted in fixed time period was determined to assess the expression of CD80, CD83 and CD86 after the binding of this double stranded DNA and fluorescent dye Sybr Green in PCR master mix. * represents the significance level p<0.05 while ** represents the significance level p<0.01. Co-stimulatory molecules CD80/CD86 are important in mDCs, the levels of them affect the natural T cell activation. CD83 is a high level cell marker in mDCs.

Figure 2:
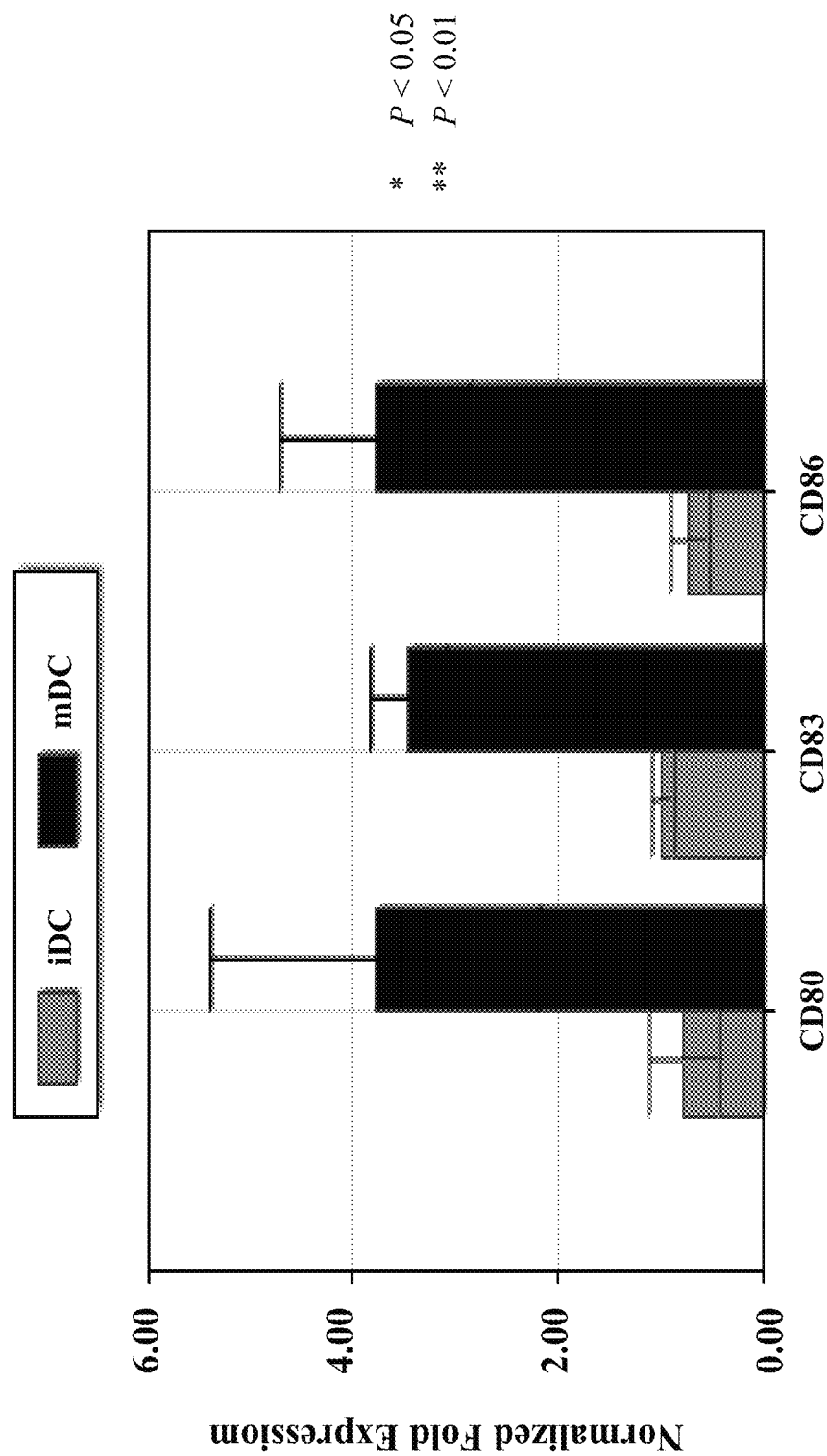
FIG. 2 shows the expression levels of CD80, CD83 and CD86 genes in bone marrow-derived mDCs and iDCs. The significance level is *$p<0.05$.
Figure 3:
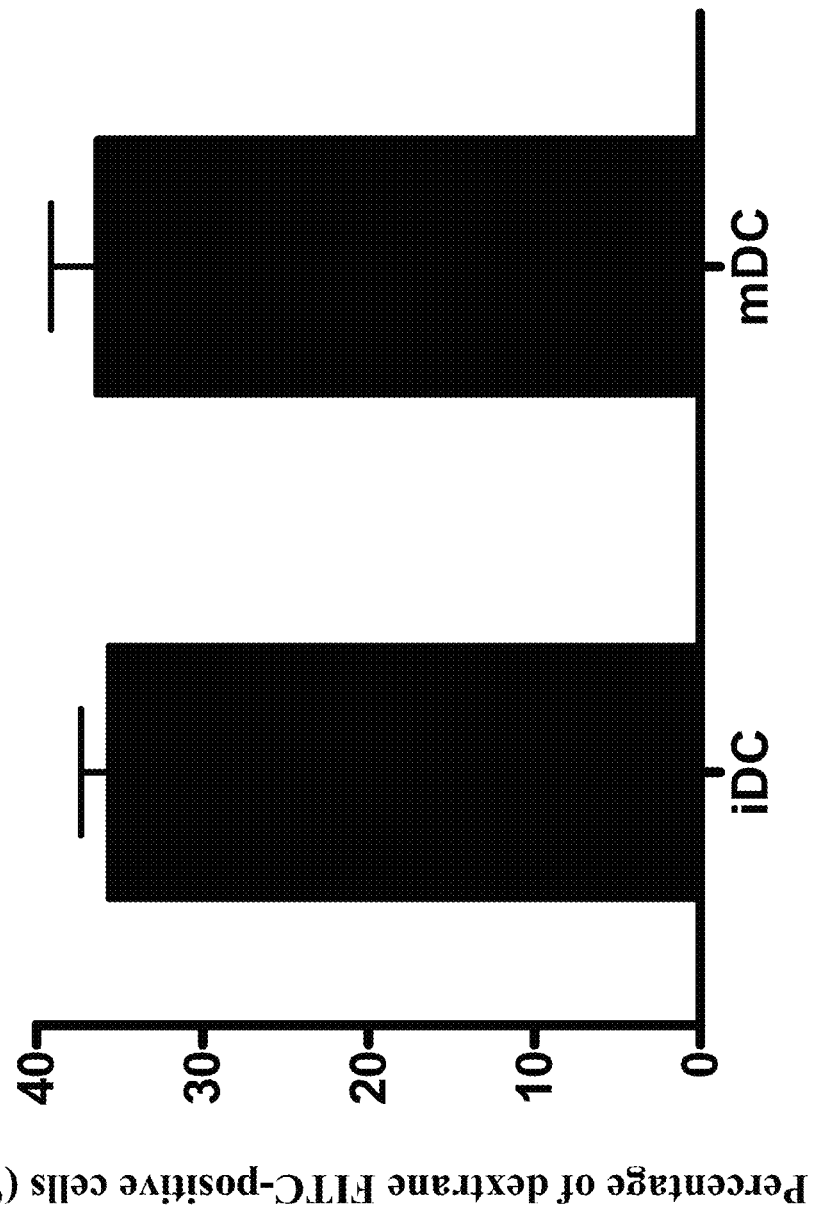
FIG. 3 shows the dextran uptake of mDCs and iDCs.
Figure 4:
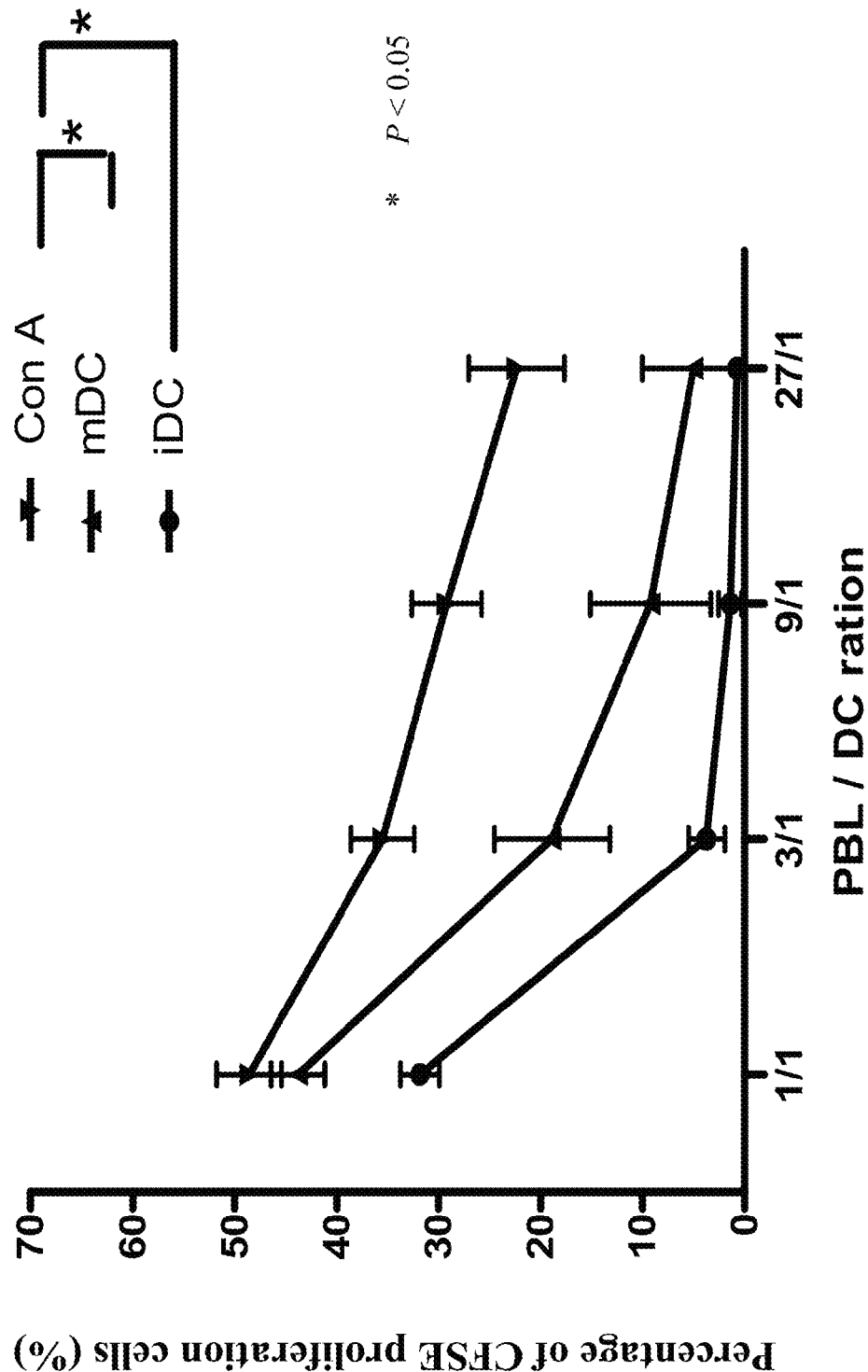
FIG. 4 shows the mixed lymphocyte reaction of mDCs and iDCs. The significance level is *$p<0.05$.

The expression of MHC II will be increased during the maturation process of iDCs. CD11c, CD40, and CD1a express in large scale in the beginning of the maturation process. The co-stimulatory molecules of CD80, CD83 and CD86 were detected by real time reverse transcription-PCR due to lack of specific antibodies of CD80, CD83 and CD86. FIG. 2 shows the increase of these co-stimulatory molecules during the maturation process. The dextran uptake and mixed lymphocyte reaction (MLR) were used to assess the physiological functions of the bone marrow-derived DCs such as antigen uptake and T cell activation ability. FIG. 3 and FIG. 4 show the results of dextran uptake and mixed lymphocyte reaction respectively. Con A is the control group (in a statistic significance of *p<0.05). mDC and iDC as mature DCs and immature DCs were cultivated with FITC-dextran for 2 h at 4° C. and 37° C., washed by PBS and analyzed the ingestion ability at 488 nm in flow cytometer. Higher level of mixed lymphocyte reaction was found in mDCs than in iDCs, while dextran uptake was not decreased. In summary, MHC II/CD11c+/CD1a+/CD40+ expressed in bone marrow-derived DCs were harvested and the antigen endocytotic ability and antigen presentation ability were demonstrated in these cells.

The CTVT fusion cells were deposited on Dec. 12, 2011 at the China Center for Type Culture Collections, Wuhan University, Wuhan 430072, P.R. China with the Accession Number C201183. The details of the establishment of the fusion cells and the corresponding test methods are described in, but are not limited to, examples as follows:

Preparation of Bone Marrow-Derived DCs a. transferring the collected bone marrow (including bone marrow cells) into a 50 ml centrifuge tube containing IMDM (transport medium supplementing with 2% of FBS and 1% of antibiotics) and mixing thoroughly; b. spinning down the cells by 400×g; c. collecting the cells (decanting the supernatant), adding 4 ml of IMDM supplementing with 2% of FBS per ml of bone marrow; d. separating the mononuclear cells with Ficoll; e. culturing the cells with a DC medium after washing cells several times; f. collecting iDCs at the $7^{th}$ day.

Other iDCs were collected at the $10^{th}$ day after adding 250 ng/ml of LPS. The composition of the DC medium is:

RPMI1640, 10% FCS, IL-4 (20 ng/ml), and Granulocyte-macrophage colony-stimulating factor GM-CSF (20 ng/ml).
PEG Fusion of CTVT and DCs a. mixing bone marrow-derived DCs and tumor cells in a ratio of 1:1; b. culturing the cells with RPMI1640 medium supplementing with 10% FCS culture for 4 to 6 h; c. washing the cells with serum free RPMI; d. collecting the cells (decanting the supernatant) after spinning down the cells, suspending the cells with micropipette in media in the order of 1000 µl, 100 µl and 10 µl to improve the fusion rate; e. adding 1 ml of polyethylene glycol (PEG) and shaking for 2 min at 37° C.; f. adding 10 ml of serum free RPMI in a proper rate for at least 5 min and shaking gently; g. spinning down the cells by 450×g; h. mixing the cells with medium containing RPMI1640, 10% FCS, and cytokine, and culturing for 3 days followed by staining with dye to observe the fusion rates and collecting the fusion cells for vaccine preparation.

The fusion cell composed of a syngeneic canine tumor cell and an allogeneic dendritic cell according to the present invention shows the following results.

1. Preparation of Hybrid Cells

Figure 5:
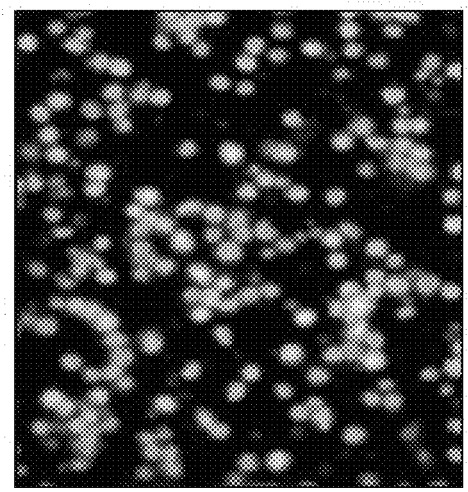
FIG. 5 shows the stained DCs, tumors and fusion cells under a fluorescent microscope. The significance level is *$p<0.05$.
Figure 5:
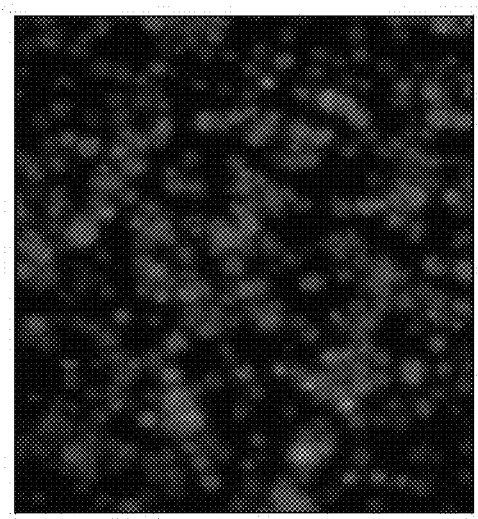
Figure 5:
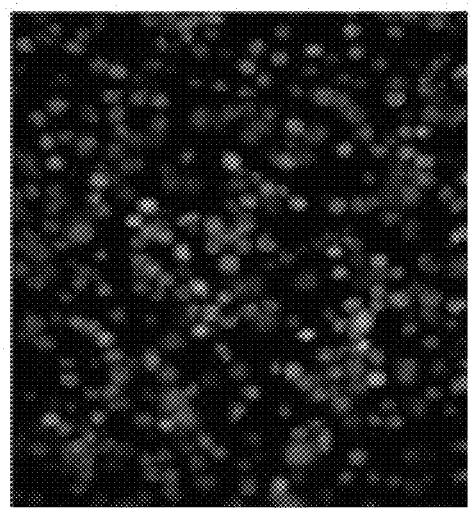
Figure 6A:
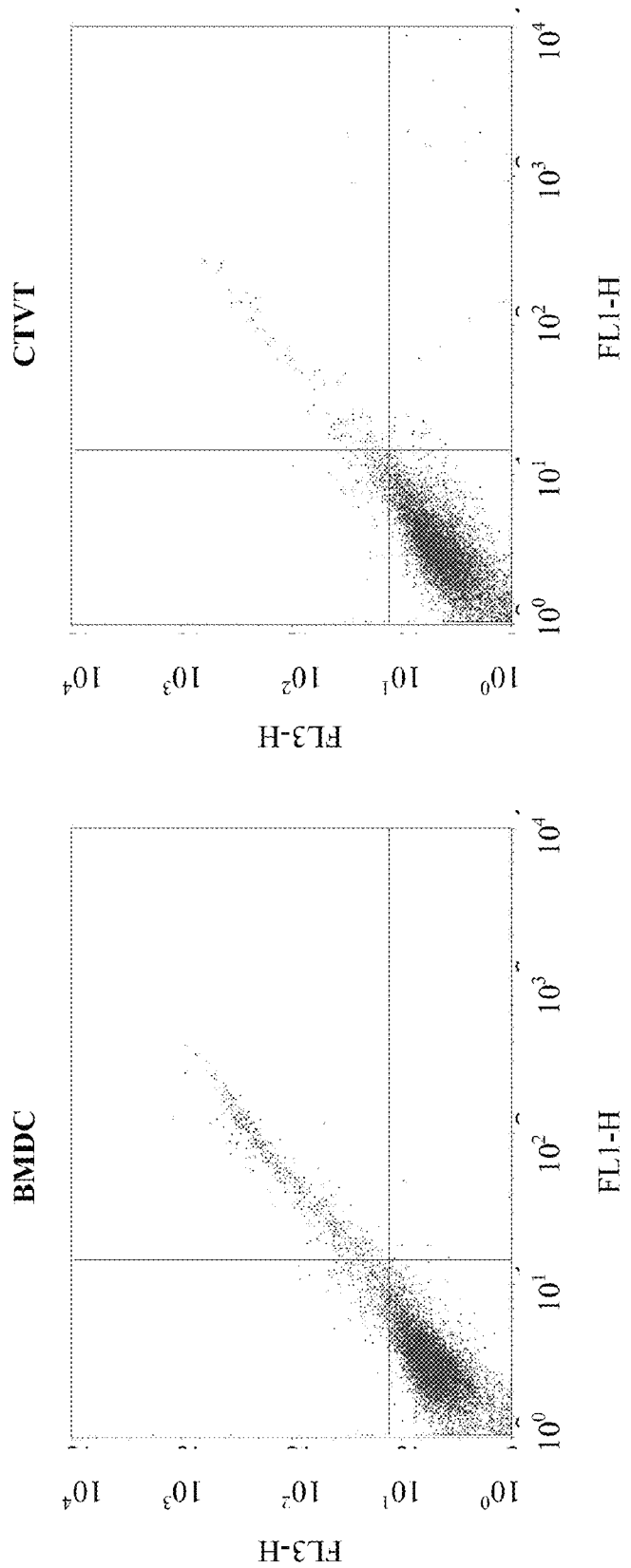
FIGS. 6A, 6B and 6C show the efficiency of fusion determined by flow cytometry.
Figure 6B:
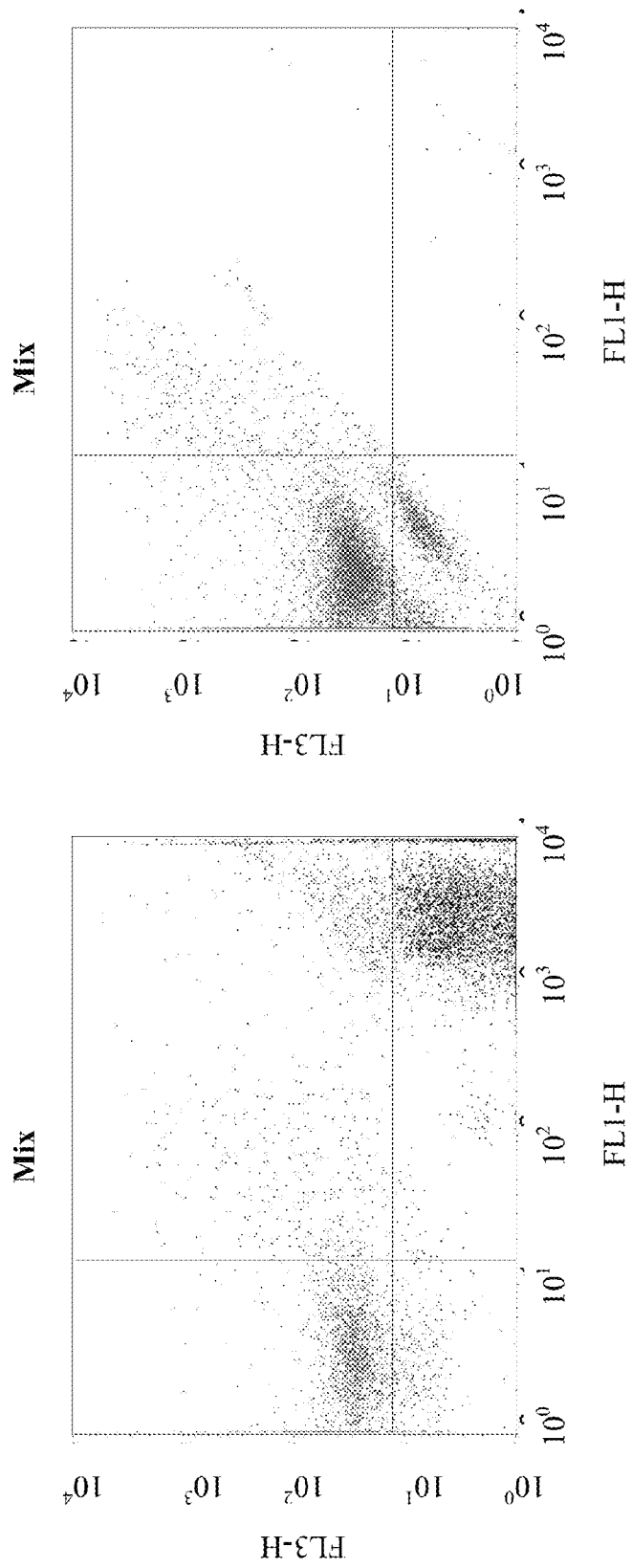
Figure 6C:
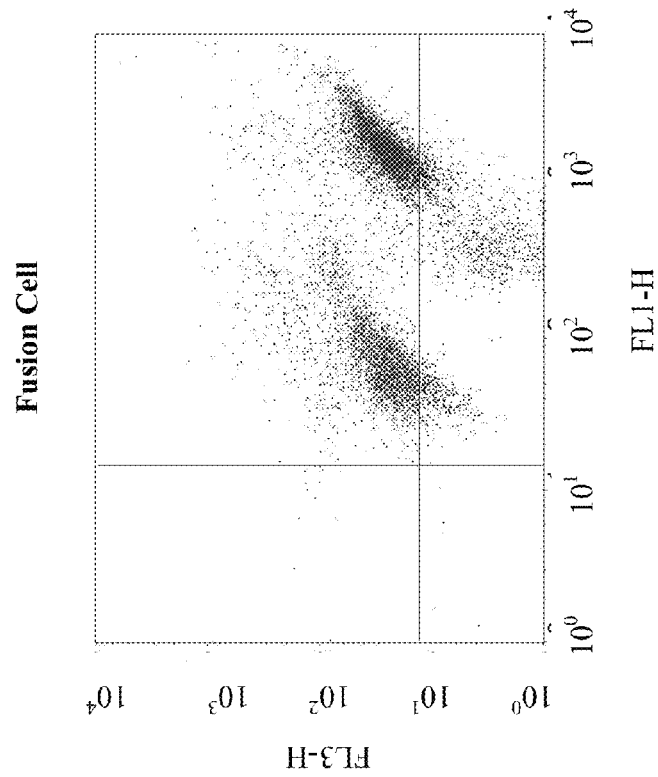
Figure 6C:
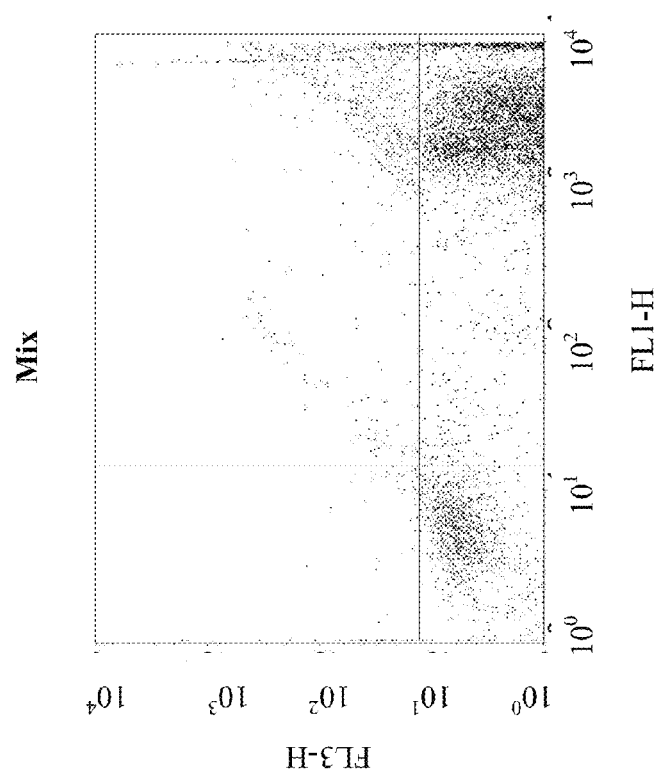
Figure 7A:
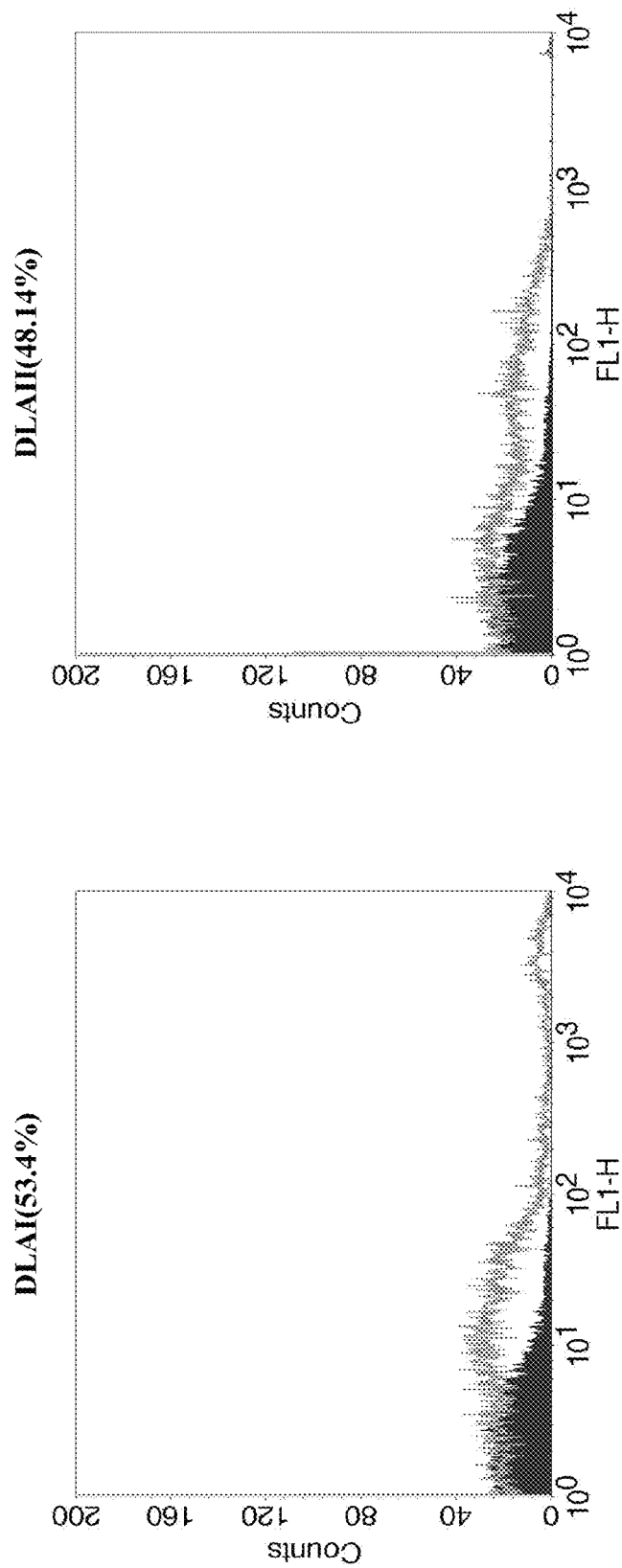
FIGS. 7A, 7B and 7C show the expression levels of DLA+/CD11c+/CD1a−/CD40−.
Figure 7B:
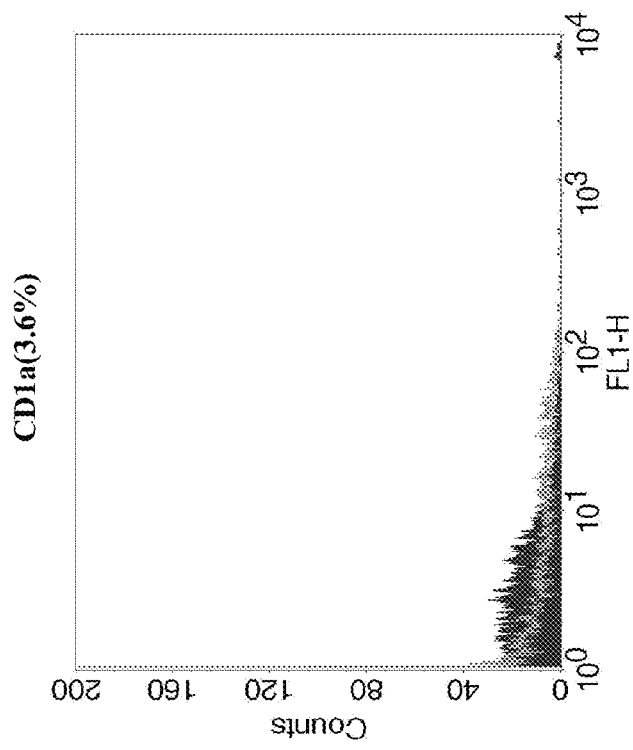
Figure 7B:
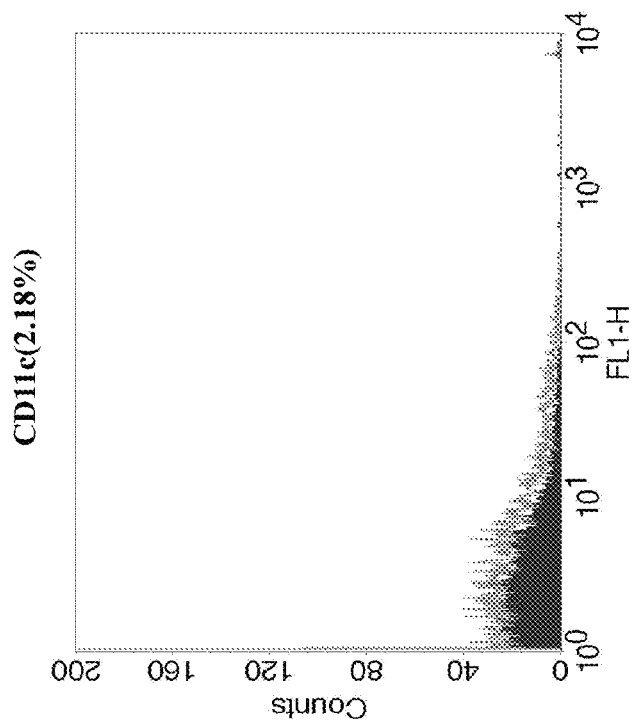
Figure 7C:
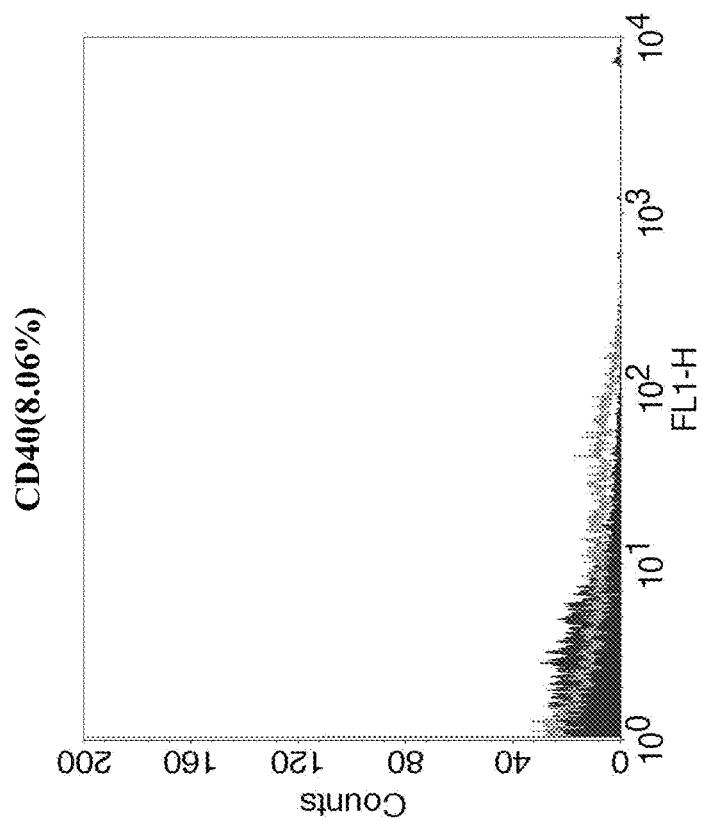

The hybrid cells used PEG in the present invention and determined the fusion rate with a flow cytometer. As shown in FIG. 5, CTCV cells were prestained in fluorescent green dye CFSE (Carboxyfluorescein succinimidyl ester), DCs were prestained in fluorescent red dye CMTPX (Cat: C-34552). PEG fused cells were observed under a fluorescent microscope using different wavelengths in the same field. The left panel shows fluorescent green with CTVT cells and the middle panel shows fluorescent red with DCs. The right panel shows fluorescent yellow with fusion cells, which displayed fluorescent both green and red after these two panels were combined. The efficiency of fusion was determined to be around 60 to 70% and showed in FIG. 6. In addition, dark area represents the isotype control while white area represents the fluorescent intensity in the experimental group in FIG. 7. The ratio of the real fluorescence stained cell in the population was determined after the dark area was deducted from the white area. The fusion cells were DLA+/CD11c+/CD1a−/CD40− after expression analysis while CTVT cells showed DLA−/CD11c−/CD1a−/CD40− because the characteristics of the fusion cells are between that of the DCs and CTVT cells.

Figure 8:
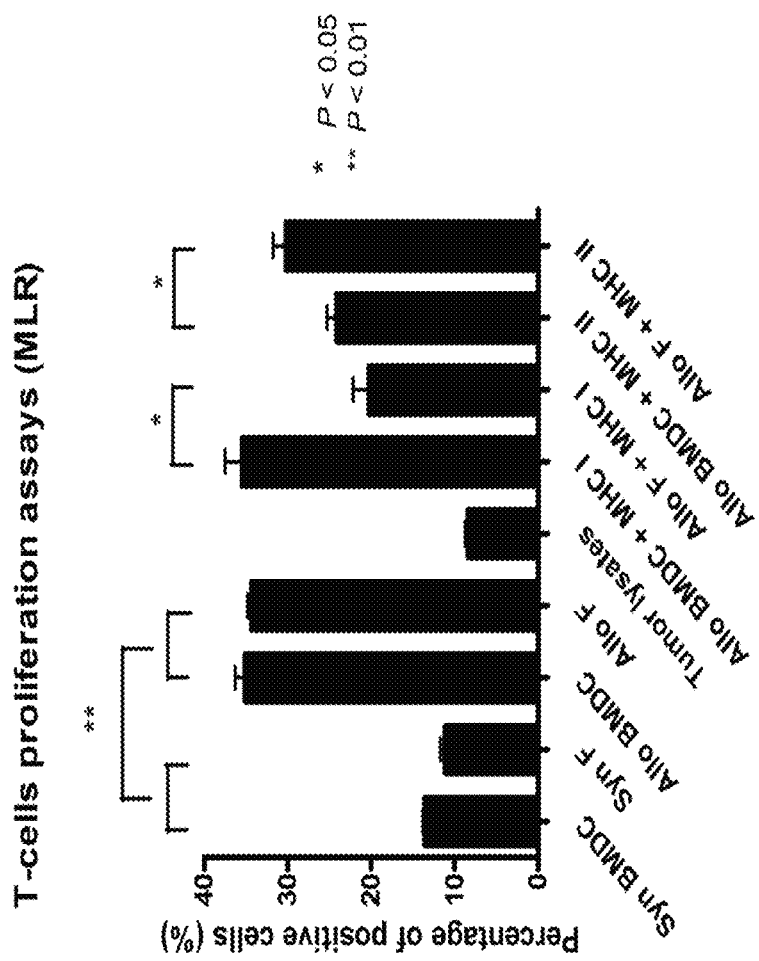
FIG. 8 shows the antigen expression levels on each tumor cells. The significance level is **p<0.01.

2. Antigen Expression Levels of the Fusion Cells after Assessed with Mixed Lymphocyte Reaction The antigen presentation ability of the fusion cells was determined by mixed lymphocyte reaction to analyze T cell dividing ability after mixing with syngeneic bone marrow derived-dendritic cells (Syn BMDC), syngeneic fusion cells (Syn F), allogeneic bone marrow derived DCs (Allo BMDC), allogeneic fusion cells (Allo F), tumor lysates, Allo BMDC+MHC I (1 µg/µl), Allo F+MHC I (1 µg/µl), Allo BMDC+MHC II (1 µg/µl), and Allo F+MHC II (1 µg/µl) respectively (FIG. 8). High antigen presenting abilities (T cell dividing ability) were shown in Allo BMDC and Allo F (allogeneic fusion cells) and were significant different from that of Syn BMDC and Syn F.

However, there is no significant difference between Allo BMDC and Allo F. That is, the antigen presentation ability was not affected by the fusion process. The fusion cells contain the antigen presentation ability and the ability to induce division of T cells. On the other hand, the major MHC II presentation process in DCs was changed into MHC I presentation process in the fusion cells.

3. Fusion Cells Clinical Assessment

Beagle dogs were evaluated clinically. The schedule of the experiment is listed in Table 2.

TABLE 2

| Study period | | Extended period[c] |
|---|---|---|
| Tumor inoculation | Treatment periods | | week 0    2nd week    4th week    5th week    6th week    7th week

Tumor inoculation    1st vaccine[b]    2nd vaccine    3rd vaccine

Sampling    Sampling    Sampling

[b]$10^8$ of hybrid cells were inject subcutaneously near the bilateral axillary and inguinal lymph nodes.
[c]2 months long time observation for regular blood and physical exams to evaluate possible toxicities.

Figure 9:
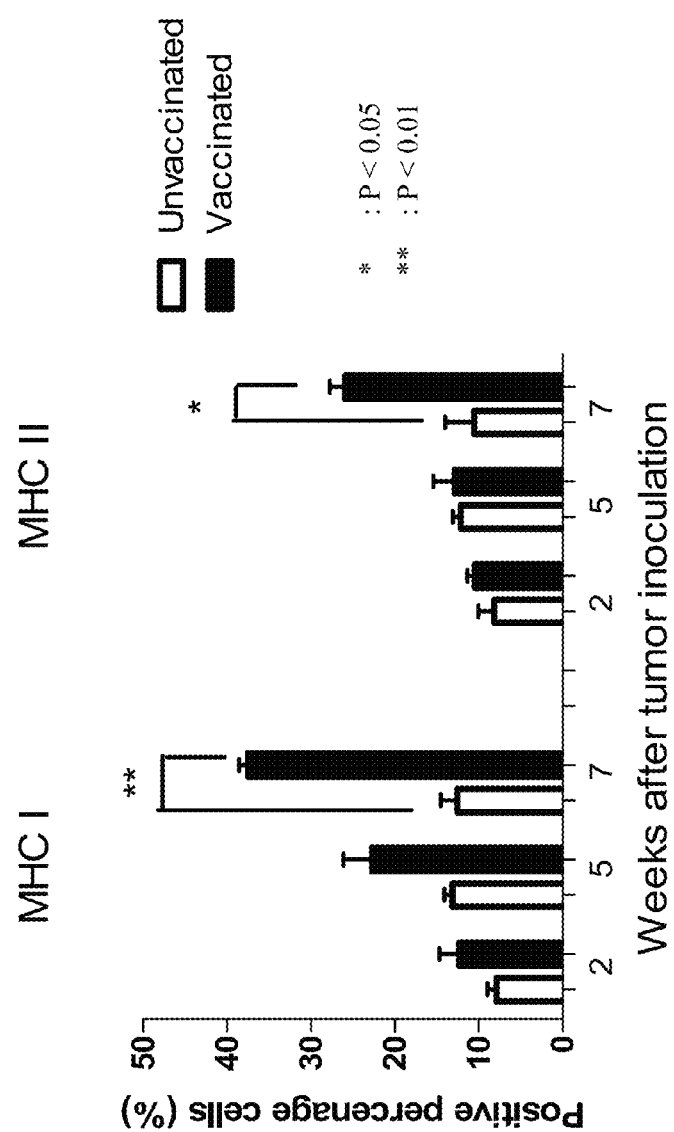
FIG. 9 shows the growth of tumor and the expression of MHC I and MHC II after inoculation of the vaccine of the present invention. The significance level * represents p<0.01, and ** represents p<0.05.
Figure 10:
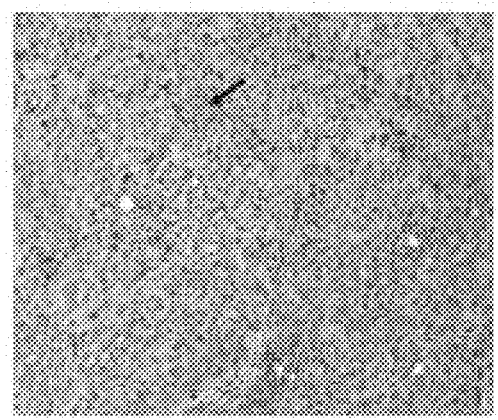
FIG. 10 shows the histopathology slide of canine tissues. Tumor infiltrate lymphocytes (TIL) is shown by arrow.
Figure 10:
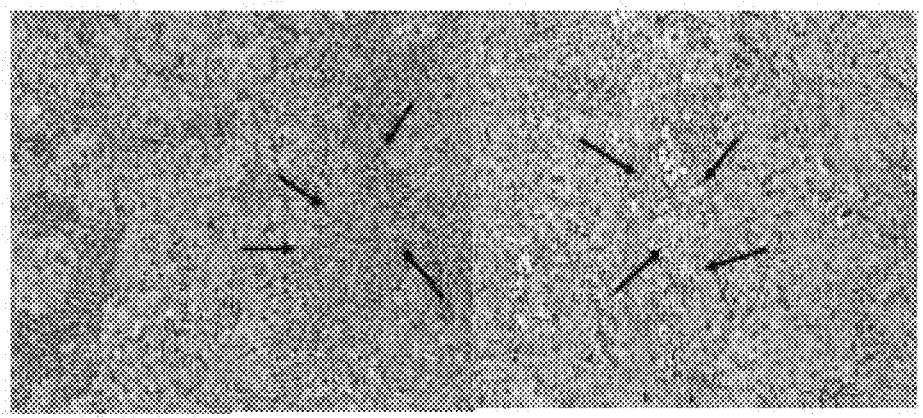

Six CTVT tumors ($10^8$ cells) were skin inoculated on the back region at a total of six sites of a healthy Beagle dog in week 0. Fusion cells were treated with Mitomycin-C before vaccination to prevent the proliferation of cells. Vaccine was injected every 2 weeks starting from the $2^{nd}$ week. The tumor was sampled and the volume was measured every 2 or 3 weeks to assess the growth of tumor and the expression of MHC. FIG. 9 shows that tumors in the vaccinated group grew slower than those in the control group. The inhibitory effect was induced starting at the second vaccine injection (the $4^{th}$ week). The tumor regression was shown in the experimental group after the third vaccine injection (the $6^{th}$ week), while tumor kept growth in the control group. The expressions of MHC I and MHC II were increased 38% and 30% with the injection of vaccine respectively in the experimental group, while they are 12% and 8% increased in the control group. Tumor infiltrate lymphocytes (TILs) were isolated and analyzed with histopathology to confirm the high level expression of MHC (FIG. 10 and Table 3). High ratio of TILs were found, and CD3, CD4, CD8 and CD21 were also increased in the experimental group. On the contrary, scarce TILs were found in the control group. Histopathological review revealed multifocal necrosis of tumor debris and high number of TILs in the experimental group, while complete tumor cells were shown in the control group. In summary, the inhibitory effects on tumors of the fusion cells were started and the expression levels of MHC were increased after the second vaccine injection. At the same time, TILs has also showed an increase trend.

TABLE 3

| Surface marker | Non-vaccinated (%) | Vaccinated (%) |
|---|---|---|
| CD3 | 0.19 ± 0.05 | 16.12 ± 3.99 |
| CD4 | 0.07 ± 0.03 | 13.55 ± 3.35 |

TABLE 3-continued

| Surface marker | Non-vaccinated (%) | Vaccinated (%) |
|---|---|---|
| CD8 | 0.08 ± 0.02 | 8.9 ± 2.25 |
| CD21 | 0 | 3.88 ± 0.75 |

Figure 11A:
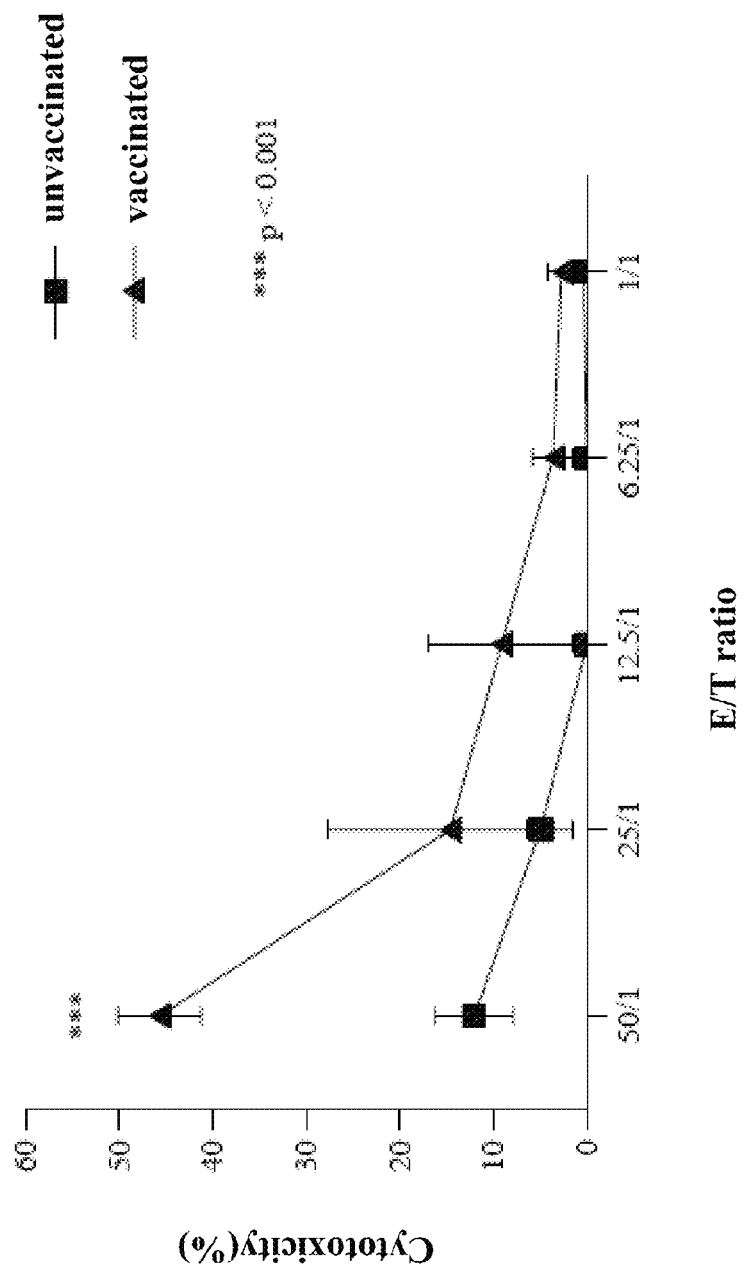
FIG. 11A shows the results of cytotoxic T lymphocyte (CTL). The significance level is ***p<0.001.
Figure 11B:
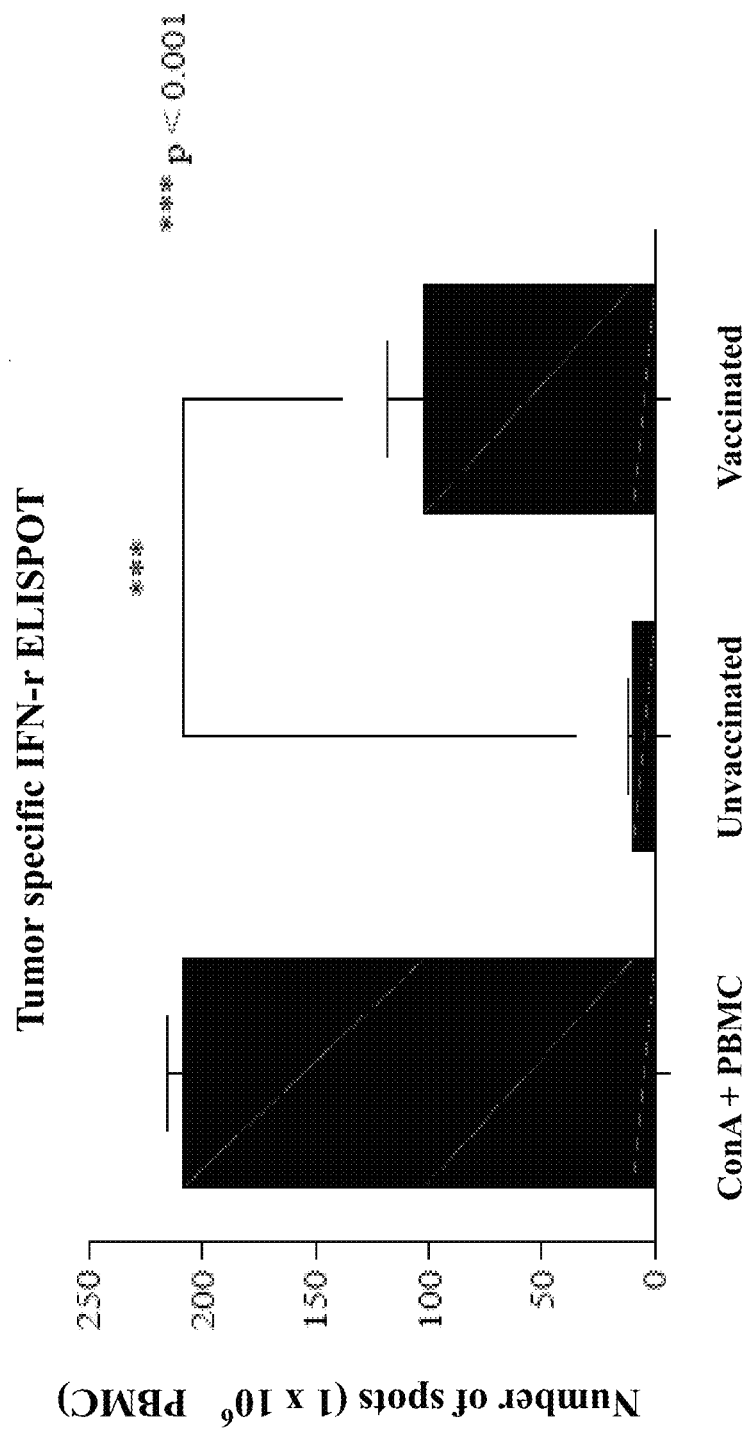
FIG. 11B shows the results of enzyme linked immuno spot (ELISPOT) analysis.

According to the results that the fusion vaccine could induce the infiltration of TILs to tumor, further study was carried out to determine tumor killing ability by the lymphocytes in dogs with tumor. Peripheral blood mononuclear cells (PBMC) were isolated from both the experimental and control groups and cultured with mitomycin-C treated tumor to perform cytotoxic T lymphocyte (CTL) and enzyme linked immuno spot (ELISPOT) analysis (FIGS. 11A & B). The cytotoxic experiment was carried out by mixing the PBMC with mitomycin-C treated tumor in a 24-well plate and culture for 6 days with 1 ml of medium changing every day. Cells were isolated with Ficoll-Hypaque density gradient centrifugation and culture in 96-well plates preload with tumors (target cells) in the ratio of 50:1, 25:1, 12.5:1 and 1:1 (stimulated lymphocytes to tumor cells) for 6 hours. The lactate dehydrogenase using CytoTox 96 non-radioactive cytotoxicity was assay at 490 nm with ELISA reader to determine the ability of tumor killing.

On the other hand, Canine IFR-γ development module kit was used in ELISPOT analysis. PBMC and tumor cells were cultured as described in CTL experiment. PBMC isolated from normal dog were served as a negative control group, while PBMC supplemented with ConA as a positive control group. The color was developed with ELISPOT kit, the number of spots were counted to determine the IFN-γ secretion.

The fusion cells indeed could induce CTL response against tumor, and tumor regression was found after therapy. The results confirmed that the fusion cells activated specific adaptive immunity. However, MHC I was expressed in only 30% of the tumor cells, which could be recognized by CTL. And the other MHC I non-expressing tumor cells were killed by natural killer cells which were induced by fusion cells. There are more natural killer cells expressed in the experimental group than in the control group (FIG. 11C). Therefore, the vaccine can also induce innate immunity such as natural killer cells.

Besides using PEG in cell fusion, electrofusion was also performed in another example of the present invention. The membrane of protoplast breaks in a snap and fuses to the neighboring protoplast, and follows by membrane closing to form hybrids in an inhomogeneous electrical field due to the unbalanced force of the electrical field. These fusion hybrids can be heterokaryons giving rise to one to one parental type, spontaneous segregants in various ratio, isogeneic protoplast homokaryon, and heterokaryon derived from different protoplasts (mostly formed from a sub-protoplast without nucleus and a protoplast with a nucleus).

On the other hand, vaccine toxicology was determined by side effects of these fusion cells. Blood samples were taken every week for toxicological evaluation. The basic diagnosis data was shown in Table 4. All the blood values were in the normal range, and dogs are in good condition and with good appetite in both the experimental and control groups. No abnormal situation was found. Therefore no side effect could be found by vaccine injection during the experimental stages.

TABLE 4

|  | Non-vaccinated | Vaccinated | Reference |
|---|---|---|---|
| Body temperature (° C.) | 39 ± 0.1 | 38.86 ± 0.05 | 38.5-39.5 |
| Hemoglobin (g/Dl) | 14.85 ± 2.38 | 17.85 ± 0.98 | 12-18 |
| WBC ($10^3$/ul) | 18466.6 ± 1965.5 | 9450 ± 650.6 | 6000-17000 |
| ALT (U/L) | 32.75 ± 6.18 | 34 ± 8.50 | 4-66 |
| BUN (mg/dL) | 10.25 ± 1.5 | 11.75 ± 2.51 | 5-28 |
| Albumin (g/dL) | 3.37 ± 0.09 | 3.2 ± 0.11 | 2.3-3.9 |
| Glucose (mg/dL) | 91.25 ± 10.21 | 95.25 ± 10.96 | 67-147 |

In summary, the fusion cells of the invention composed of allogeneic bone marrow-derived dendritic cells and canine CTVT tumor cells, which can be used as canine CTVT vaccine, and can induce the canine immune system to defend against canine tumor growth.

What is claimed is:

1. A fusion cell (CCTCC C201166) composed of a canine transmissible venereal tumor cell and an allogeneic dendritic cell, which is based on expression of a canine tumor antigen to induce the proliferation of tumor specific T lymphocytes and natural killer (NK) cells in canine immune system.

2. A vaccine for treating canine transmissible venereal tumor comprising the fusion cell of claim 1.

3. A method for preparing a fusion cell composed of a canine transmissible venereal tumor cell and an allogeneic dendritic cell comprising:
   (a) isolating a mononuclear cell from a canine bone marrow and culturing the mononuclear cell to an immature dendritic cell;
   (b) culturing the immature dendritic cell to form a mature dendritic cell;
   (c) mixing the mature dendritic cell and the canine transmissible venereal tumor cell to form a cell culture; and
   (d) applying electrofusion to the cell culture to form the fusion cell.

4. The method as claimed in claim 3, wherein the step (a) further comprises culturing the mononuclear cell with a DC medium containing RPMI 1640, 10% FCS, IL-4 and GM-CSF.

* * * * *